United States Patent [19]
Cotrel

[11] Patent Number: 5,899,903
[45] Date of Patent: May 4, 1999

[54] FIXING DEVICE FOR A RIGID TRANSVERSE CONNECTION DEVICE BETWEEN RODS OF A SPINAL OSTEOSYNTHESIS SYSTEM

[75] Inventor: Yves P. Cotrel, President Wilson, France

[73] Assignee: Sofamor, S.N.C., Cedex, France

[21] Appl. No.: 09/067,680

[22] Filed: Apr. 28, 1998

Related U.S. Application Data

[63] Continuation of application No. 08/690,811, Aug. 1, 1996, Pat. No. 5,743,911.

[51] Int. Cl.[6] .................................................. A61B 17/70
[52] U.S. Cl. ................................. 606/61; 606/72; 606/73
[58] Field of Search ................................. 606/60, 61, 72, 606/73

[56] References Cited

U.S. PATENT DOCUMENTS

| | | | |
|---|---|---|---|
| 3,499,222 | 3/1970 | Linkow et al. | 13/22 |
| 4,257,409 | 3/1981 | Bacal et al. | 606/61 |
| 4,567,884 | 2/1986 | Edwards | 606/61 |
| 4,716,894 | 1/1988 | Lazzeri et al. | |
| 4,773,402 | 9/1988 | Asher et al. | 606/61 |
| 5,102,412 | 4/1992 | Rogozinski | 606/61 |
| 5,275,600 | 1/1994 | Allard et al. | 606/61 |
| 5,374,267 | 12/1994 | Siegal | 606/61 |
| 5,522,816 | 6/1996 | Dinello et al. | 606/61 |
| 5,527,314 | 6/1996 | Brumfield et al. | 606/61 |
| 5,601,552 | 2/1997 | Cotrel . | |
| 5,624,442 | 4/1997 | Mellinger et al. | 606/61 |

FOREIGN PATENT DOCUMENTS

| | | |
|---|---|---|
| 0446092 | 9/1991 | European Pat. Off. . |
| 2 645 427 | 10/1990 | France . |
| 2645427 | 10/1990 | France . |
| 2659225 | 9/1991 | France . |
| 3219575 A1 | 1/1983 | Germany . |
| 3219575 A1 | 12/1983 | Germany . |
| 825942 | 5/1981 | Russian Federation . |

OTHER PUBLICATIONS

English document purporting to be a translation of Russian Patent No. 825842.

Proported translation of French Patent Application No. 2,645,427 Inventor: Cotrel; Filed: Oct. 12, 1990.

*Primary Examiner*—Michael Buiz
*Assistant Examiner*—Daphna Shaz
*Attorney, Agent, or Firm*—Woodard, Emhardt, Naughton, Moriarty & McNett

[57] ABSTRACT

The body (4) of the hook (1) has a passage (6) for receiving a transverse bar, which passage terminates in an aperture (7) and extends throughout the length of the body. The hook (1) includes a curved strip portion (5) for retaining an osteosynthesis rod which is connected to the body (4) in a region of said aperture (7). The height of the aperture (7) exceeds the thickness of the bar. The strip portion (5) has a width substantially equal to the width of the body (4) and edge portions (9) of the passage (6) are so shaped as to define sliding ramps for the rod which are inclined toward the interior of the strip portion (5). The arrangement of the hook ensures a trapping of the rod which improves the safety of the device in use and reduces the overall size of the hook.

9 Claims, 6 Drawing Sheets

*Fig. 15*

FIXING DEVICE FOR A RIGID TRANSVERSE CONNECTION DEVICE BETWEEN RODS OF A SPINAL OSTEOSYNTHESIS SYSTEM

This application is a continuation of application Ser. No. 08/690,811 filed on Aug. 1, 1996 now U.S. Pat. No. 5,743,911.

The present invention relates to a fixing device for a transverse connection device for ensuring a rigid connection between two rods of a spinal osteosynthesis system, by cooperation with a rigid transverse bar and a clamping of a rod against the bar.

It is known that spinal osteosynthesis instrumentation devices are usually constituted by two rods fixed to the vertebral column by hooks or screws and interconnected by transverse bars which impart to the assembly a general frame arrangement. This must have sufficient mechanical resistance to permanently afford the desired support to the vertebral column of the patient.

French patent 2 645 427 filed under No. 89 04 750 discloses a transverse bar whose two end portions are curved toward each other so as to form hooks for receiving the rods. However, this very simple arrangement has not given the expected results, in particular owing to the lack of possibility to act on the rods themselves by moving them away from or toward each other. Indeed, this has required the provision of a sufficient number of standard transverse bars in which the distances between the axes of the curved ends forming the hooks are different. But this does not solve the problem of the intermediate dimensions for which this device cannot be used.

French patent 2 659 225 filed under No. 90 02 970 discloses a transverse connection device comprising a bar having a rectangular section straddled by independent hooks. Each hook has a body and two strip portions spaced apart by a gap whose width corresponds to that of the bare each strip portion being consequently placed on each side of the bar when the hook straddles the latter. But, in order to obtain a sufficient mechanical resistance, each strip portion must have a certain width. The width of the strip portions added to that of the gap for the passage of the bar results in an overall size which cannot be reduced.

Now, one of the constant concerns of surgeons in the field of spinal osteosynthesis is the reduction in the overall size of the parts employed with no reduction in their mechanical resistance. Indeed, even a small reduction in the overall size, i.e. measured in millimeters or even fractions of a millimeter is of obvious interest.

An object of the invention is therefore to provide a fixing hook which has a reduced overall size relative to that of known hooks and yet retains excellent mechanical properties and moreover provides excellent safety as concerns the fixing of the rod against risk of the connection coming apart.

According to the invention, a passage for receiving the bar is provided longitudinally in the body of the hook. This passage has a height which is at least equal to the thickness of the bar, extends throughout the length of the body and freely opens out at both ends. This is why the end of the body of the hook connected to its strip portion has an aperture which is located in the extension of the passage receiving the transverse bar and has a height which exceeds the thickness of said bar.

Further, the passage aperture for the bar allows the latter a freedom of angular movement which facilitates the mounting of the device (which it must be recalled is carried out under the circumstances of a delicate surgical operation) and therefore permits adjusting its orientation and/or its position with more precision.

In the hook disclosed in the patent 2 659 225, the recesses enabling the hook to be taken hold of by the accessory are provided at the opposite ends of the body of the hook, in the direction of the bar, so that they are necessarily located above the latter and consequently increase the overall height of the hook. In a possible embodiment of the hook according to the invention, these recesses are provided on the lateral faces of the bar, substantially in the region of the surface of the latter. Consequently, there is a substantial reduction in the overall height of the body of the hook approximately equal to the width of the recesses, namely on the order of a millimeter.

According to another feature of the invention, the body of the hook is extended by an inwardly curved strip portion for retaining and clamping the associated rod, said aperture being formed in a region of connection of the body to the strip portion, and the latter has a width substantially equal to the width of the body of the hook.

According to another feature of the invention, the edge portions of the passage of the hook body are so shaped as to define sliding ramps for the rod which are inclined toward the interior of the strip portion so as to facilitate placing the rod in the curved part of the strip portion, the inclination of these ramps relative to the transverse bar being at a few degrees.

In a particularly advantageous embodiment of the hook, the tapped hole and the clamping screw are positioned in the body of the hook in such manner that the axis of the screw is located between an axial plane of the rod parallel to the axis of the screw and a plane tangent to the surface of the rod located in the open part of the hook, parallel to the axis of the screw and to said axial plane, this axis of the screw being for example located at about two-thirds of the distance between said two parallel planes measured from said axial plane.

Further features and advantages of the invention will be apparent from the following description, with reference to the accompanying drawings which illustrate various embodiments of the invention given by way of non-limitative examples.

The fixing hook 1 shown in the drawings is a part of a rigid transverse connection device interconnecting two rods 2 of a spinal osteosynthesis system (FIG. 5), by cooperation with a rigid transverse bar 3 and a clamping of a rod 2, associated with each hook 1, against the bar 3. The latter has an adapted section, for example a rectangular or a circular section, which is constant throughout its length in the presently described embodiment.

Figure 5:
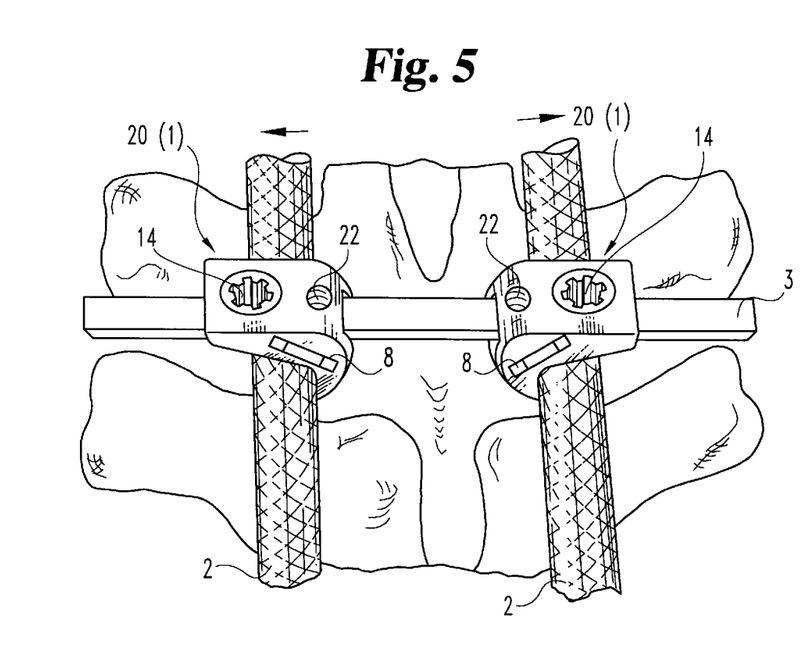
FIG. 5 is a perspective view of a transverse connection device comprising two hooks according to a second embodiment of the invention, a bar and two rods, mounted on a spinal segment in which the two rods are spread apart.

Each of the two hooks 1, which may be part of the transverse connection device shown in FIG. 5, comprises a body 4 and a single strip portion or lug 5 which is curved inwardly in the direction toward the body 4 with which it is in one piece. Provided in the body 4 is a passage 6 for receiving the bar 3, this passage having a height h which is at least equal to the effective thickness of the bar 3.

The passage 6 opens out at the ends of the body 4 and, on the side of the body 4 extended by the curved strip portion 5, terminates in an aperture 7 whose height H exceeds the thickness of the bar 3. In the illustrated embodiment, the height H is about twice the thickness of the bar 3. This numerical indication is not intended to be limitative.

Edge portions 9 constituting walls of the body 4 defining the passage 6 are each so shaped as to define a rectilinear sliding ramp 11 for the associated rod 2, are inclined toward the interior of the strip portion 5 and are connected to a first concave region 12 of the strip portion. Each ramp 11 has a suitable inclination relative to the rectilinear bottom of the passage 6, i.e. to the transverse bar 3 when the latter is applied against the bottom of the passage 6. Consequently, the passage 6 has a depth which increases from h to H, i.e. from the end thereof remote from the strip portion 5 to the aperture 7.

Figure 2:
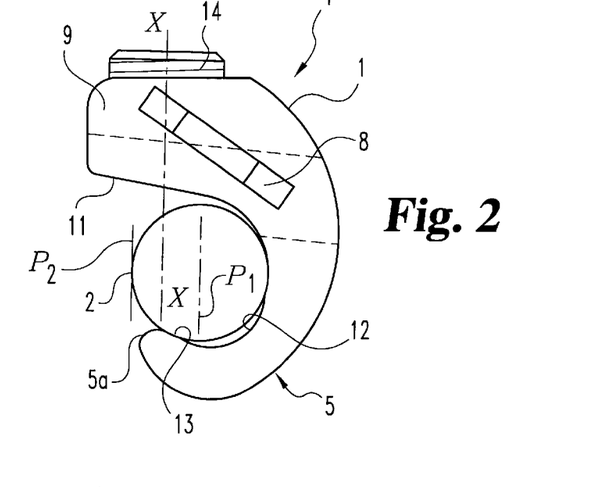
FIG. 2 is a side elevational view, to a large scale, of the hook shown in FIG. 1 in which the spinal osteosynthesis rod is inserted.

The curved region 12 has a radius of curvature r1 (FIG. 3) which is equal, or substantially equal, to the radius of the cylindrical rod 2 (which may have asperities or knurling as shown in FIG. 5 or be smooth), and this region 12 is followed, in the direction toward the rounded free end portion 5a of the strip portion 5, by a second curved region 13 which rises toward the body 4. This concave region 13 has, in the embodient shown in FIGS. 2 and 3, a radius of curvature r2 which is substantially equal to the radius of curvature r1, but its centre of curvature $0_2$ is slightly offset from the centre of curvature $0_1$ of the region 12 toward the interior of the hook 1. Thus the region 13 and the free end portion 5a are slightly raised in the direction toward the body 4 relative to a single curvature whose radius would be equal to r1. It is understood that in the specific illustrated embodiment the rod 2 is received in the region 12. The present invention also contemplates a non-circular rod 2, or even the rectangular bar 3 being engaged within the region 12, with the region being linear or flat rather than curved.

Recesses 8 for the handling of the hook 1 by an accessory (known per se and not shown), are provided on the lateral faces of the body 4 which are parallel to each other. These recesses or grooves 8 have a concavity in the transverse direction, i.e. toward the interior of the walls of the body 4, the radius of curvature of these two concavities being identical to that of the convexity of the corresponding impression provided on the end portions of the holding accessory.

The recesses 8 are oblique with respect to the upper face of the body 4 of the hook so as to clear the space required for the tool screwing the screw 14.

The radius of curvature r2 may be substantially smaller than r1, in which case its centre of curvature may coincide with $0_1$. It is also possible to replace the concave region 13 by a planar surface inclined at a suitable angle, or arrange this inclined planar surface at the end of the region 13, between the latter and the rounded end portion 5a. Such an inclined planar surface may have a width of 2 to 3 mm so as to constrain the rod 2 to slide at the bottom of the groove defined by the strip portion 5.

Figure 1:
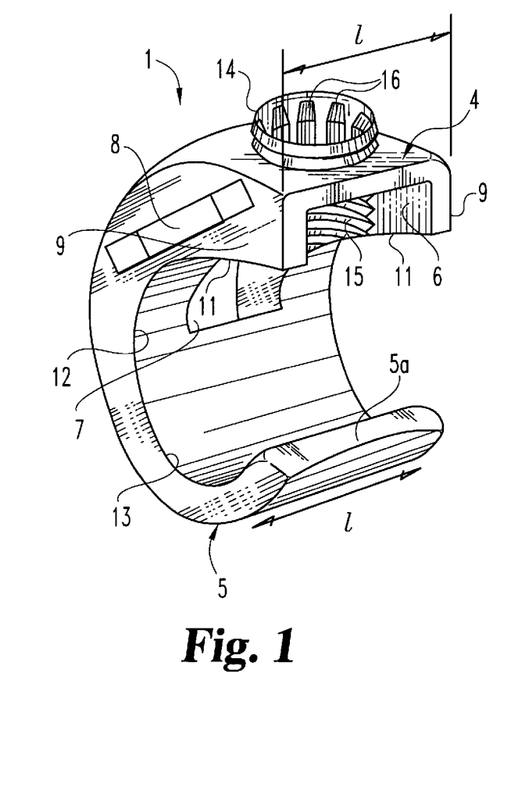
FIG. 1 is a perspective view, to a large scale, of a first embodiment of the fixing hook for the transverse fixing device according to the invention.
Figure 3A:
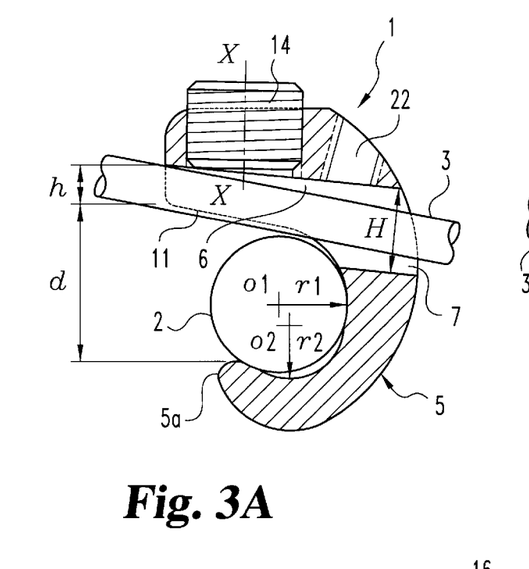
FIG. 3A is a sectional view of the hook shown in FIG. 2 and an elevational view of a transverse bar assembled with this hook and with an osteosynthesis rod, before clamping by means of a clamping screw inserted in the hook.

The hook 1 is provided with a screw 14 for clamping the bar 3 of the rod 2, this screw 14 being inserted in a tapped hole 15 provided in a wall of the body 4 interconnecting its two lateral walls 9 and opening onto the passage 6. The tapped hole 15 is so positioned that is axis X—X is close to the free end portion 5a of the strip portion 5, i.e. to a plane tangent to the latter (FIG. 3A). The screw 14 may be for example a screw having a hexagonal head or constituted by a portion of a cylinder in the inner wall of which are formed impressions 16 (FIG. 1) adapted to be cooperative with a corresponding screwing tool (known per se and not shown).

Figure 7:
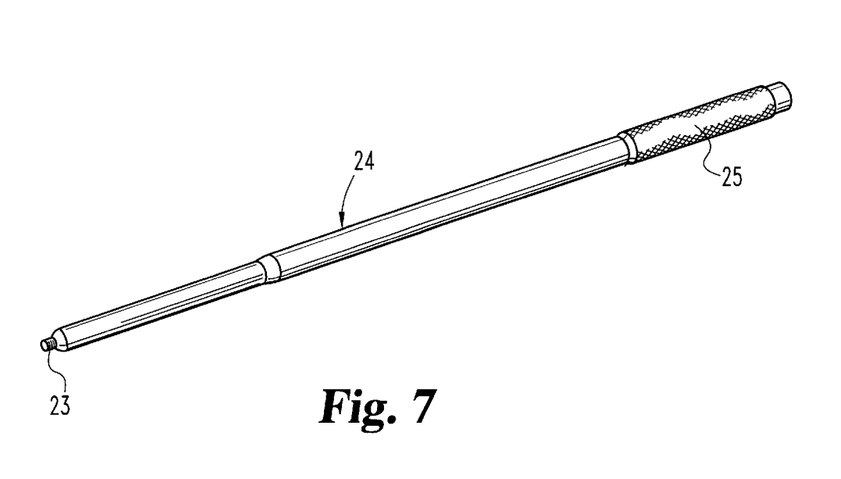
FIG. 7 is a perspective view of the accessory for handling the hook shown in FIG. 6.

Provided in the curved part of the body connecting the aperture 7 to the tapped hole 15 between the clamping screw 14 and the aperture 7, is a second tapped hole 22 whose diameter is less than or equal to that of the tapped hole 15. The tapped hole 22 is adapted to receive a corresponding screw threaded end portion of an accessory 24 (FIG. 7) consisting of a rod whose end portion remote from the terminal portion 23 constitutes a preferably knurled hand grip 25. After the screw threaded portion 23 has been screwed in the tapped hole 22, the accessory 24 is firmly fixed to the hook 20.

The recesses 8 afford the surgeon a second manner of taking hold of the hook 20, by means of a hook-carrying forceps (of known type and not shown). It will be observed that the provision of the tapped hole 22 in a sufficient thickness of the body 4.3 is made possible by the inclination, relative to the planar surface 10 of the body 4.3, of the wall 6a of the passage 6 (which feature also exists in the hooks 20.1 and 20.2 shown in the FIGS. 8 and 9).

The hook 1, the bar 3 and the rod 2 are assembled in the following manner.

The surgeon mounts a hook 1 on the transverse bar 3 (having a rectangular or square section corresponding to the section of the passage 6), then passes this hook under one of the rods 2 (FIG. 3A). The bar 3 is flush with the lower end of the body 4, i.e. the end of each ramp 11. Conseguently, the bar 3 does not reduce the width of the gap d for inserting the rod 2 between the ramps 11 and the free end portion 5a of the strip portion 5. The hook 1 is so dimensioned that the width d of this gap is at least substantially greater than the total diameter of an osteosynthesis rod 2 having asperities of the type known under the name "Cotrel rod" (registered trademark). As already mentioned, this rod may of course have a smooth surface.

Figure 3B:
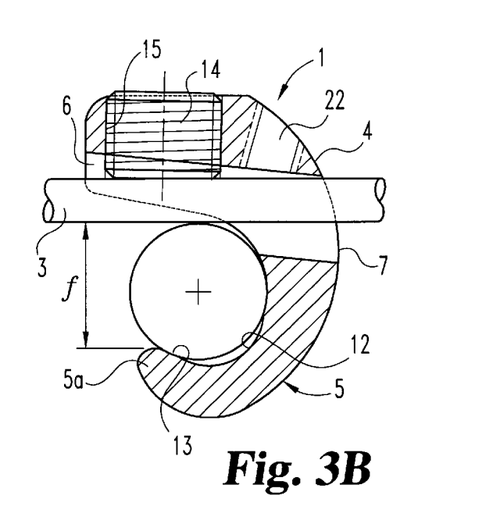
FIG. 3B is a view similar to FIG. 3A after the bar has been clamped against the rod by means of the screw of the hook.
Figure 4:
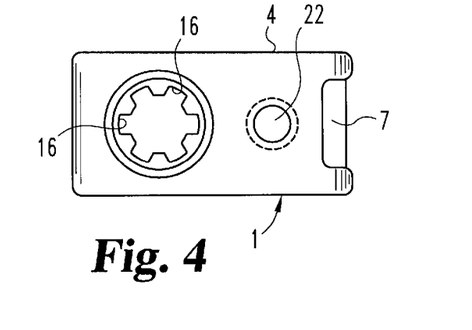
FIG. 4 is a top plan view of the hook shown in FIGS. 1 to 3B.

The surgeon slides the rod 2 on the guide ramps 11 which bring this rod to a position of contact with the first concave region 12 (FIG. 3A). As the rod 2 continues its travel, it then comes to bear against the second concave region 13 (FIG. 3B). The surgeon screws the screw 14 in the tapped hole 15.

The bearing of the screw 14 against one of the faces of the bar 3 then causes the hook 1 to tilt about the rod 2, as shown in FIG. 3B. This tilting is made possible by the dimensions of the end aperture 7 of the passage 6. Subsequent to the tightening of the screw 14, the rod 2 is clamped between the raised free end portion 5a of the strip portion 5 and the bar 3. The dimensions of the hook 1, bar 3 and rod is such that, when the three elements are assembled, the distance f between the free end portion 5a and the bar 3 is less than the diameter of the rod 2.

Figure 6:
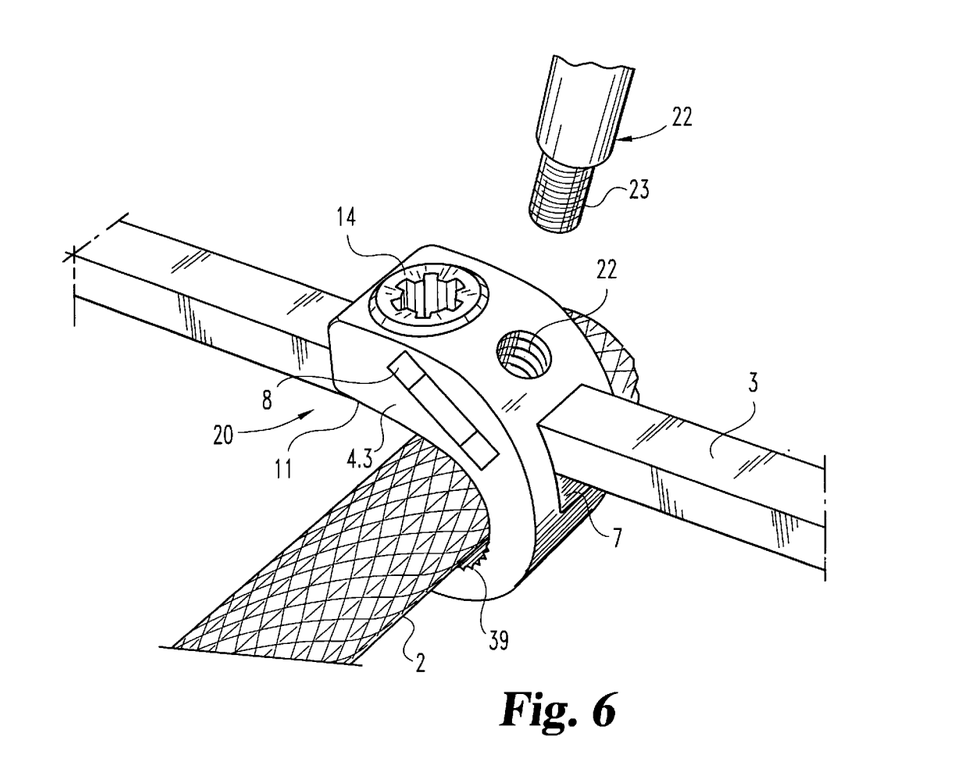
FIG. 6 is a perspective view, to a large scale, of a hook according to a second embodiment of the invention, on which the associated rod and transverse bar are mounted.
Figure 10:
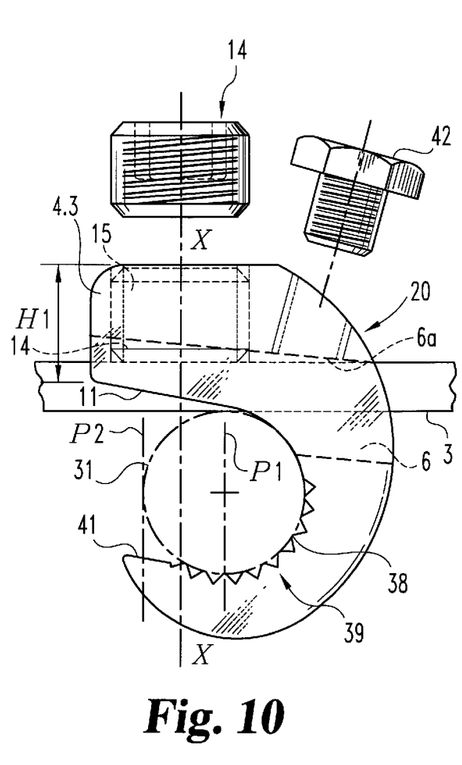

The whole of the transverse connection device between two osteosynthesis rods 2 is as shown in FIG. 5 after the mounting of two hooks (hooks 20, described hereinafter with reference to FIGS. 6 and 10, are shown in FIG. 5) on two rods 2 and a transverse bar 3. Note that the hooks shown in the spread apart position in FIG. 5 may also be placed in a position in which they are closer together in which their strip portions are oriented toward each other.

The tightening of the screw 14 causes the bar 3 to be lowered relative to the passage 6 to a projecting position relative to the edge portions 11, and also causes the hook 1 to tilt on the bar 3.

Thus, when the hook 1 is not mounted on the bar 3, or not clamped on the latter, the useful height d for inserting the rod 2 in the hook 1 exceeds the diameter of this rod. After the bar 3 has been inserted in the hook 1 and clamped on the rod 2, the height d is brought back to the value f which is less than the diameter of the rod 2.

It will be understood that the arrangement of the hook 1 thus permits trapping the rod 2 between the strip portion 5 and the bar 3 so that there is practically no risk of ejection of the rod due to movements of the patient, and resulting in an increased safety in the use of the device.

The hook according to the invention also has the following advantages:

The presence of the aperture 7 in the region of the connection between the body 4 and the strip portion 5 allows the bar 3 to move angularly, which facilitates the full mounting of the device for placing the second hook 1 in an operational region whose access is difficult and encumbered. This aperture 7 also enables the transverse bar 3 to descend under the clamping action exerted by the screw 14 so that the bar comes into contact with the rod 2. The bar 3 then traps the rod 2 in the space defined by the curved portion formed by the strip portion 5, by reducing the height of insertion defined by the body 4 of the hook and the free end portion 5a (d shown in FIG. 3A) to a dimension (f shown in FIG. 3B) which is less than the diameter of the rod 2. It will be understood that this advantage is obtained on condition that the diameter of the rod is larger than the distance between the bottom of the strip portion of the hook and the lower edge of the aperture, and that a screw 14 of sufficient length is used.

The fact that the hook 1 has a single curved strip portion 5 instead of two strip portions astride the transverse bar as in said patent 2 659 225, and that this strip portion has a width l equal to that of the body 4, imparts great mechanical resistance to the strip.

In addition to affording a connection of excellent quality, the hook according to the invention permits the realization of a transverse connection device which is very easy to mount, with a reduction in the overall size of the hook relative to prior hooks and in particular that disclosed in said patent 2 659 225, without reducing the mechanical resistance. As already mentioned, this reduction in the overall height is achieved by the combination of the suitably dimensioned passage 6 and the positioning on the lateral faces of the body 4 of the recesses or impressions 8 allowing the accessory to take hold of the hook. In the transverse direction, the width of the hook 1 is correspondingly reduced owing to the fact that the two strip portions of said patent 2 659 225 have been replaced by a single strip portion.

Thus, the connection obtained between the transverse device and the hooks 1 is considerably improved relative to the known transverse devices, in respect of the following points which were heretofore difficult to conciliate: facility of mounting, mechanical quality of the connection, mechanical resistance, safety and reliability, and reduction in the overall size. This reduction in the dimensions of the hook may be for example, in width, around 2 mm, and, in height, around 1 mm relative to the hook disclosed in said patent 2 659 225.

The disposition of the recesses or impressions 8 permits a self-centering of the impressions of the accessory and this considerably facilitates the holding of the hook 1 by the accessory owing to the excellent quality of the connection. It should also be mentioned that the lateral arrangement of the holding recesses or grooves 8 which then extend in a direction perpendicular to the axis of the rod 2, prevents any untimely rotation of the hook 1 on itself when mounting. This arrangement therefore contributes to a satisfactory mounting of the hook.

The connection achieved by means of the hook according to the invention is universal in that it can be used on a rod 1 of variable diameter within the limit of the opening of the hook and of the distance between the bottom of the strip portion and the lower edge of the aperture, which is a very important point. If the rod 2 moreover has a smooth surface instead of the type having asperities (Cotrel rod, screw threaded rod, etc.), the mechanical quality of the connection and the trapping of the osteosynthesis rod 2 obtained by means of the invention remain sufficient whatever the type of rod (smooth rod, or rod having asperities: Cotrel rod or screw threaded rod).

In the previously-mentioned alternative embodiment in which the fre end portion of the strip portion 5 of the hook 1 defines an inclined planar surface, the latter cooperates with the clamping screw 14 of which the thrust causes a sliding of the rod 2 on this inclined surface to the bottom of the groove of the hook. This thrust is transmitted to the part of the bar 3 opposite the free end portion 5a so that this part of the bar 3 maintains the osteosynthesis rod 2 firmly trapped in the hook. The thrust transmitted to the rod 2 is indeed so directed that the rod safely positions itself on the concave region 13.

The manner in which the hook 20 is taken hold of by the accessory 24 can facilitate the handling when the overall size of the forceps which hold the hook by means of the grooves is excessive.

The accessory 24 is firmly fixed to the hook 20 by the screw threaded connection of the end portion 23, which facilitates the handling of the hook when it is mounted by the surgeon on the rods.

Figure 8:
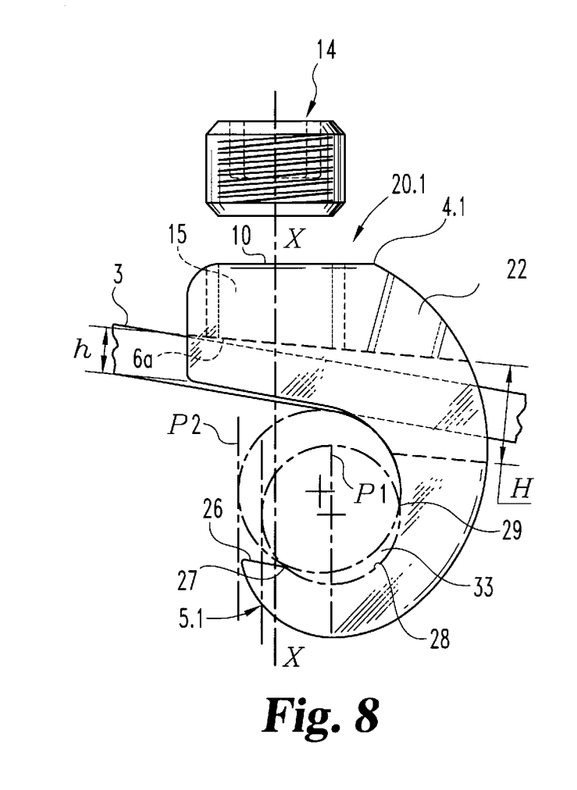
FIGS. 8, 9 and 10 are side elevational views of three possible alternative embodiments of the hook shown in FIG. 6.

In the alternative embodiment of the hook 20.1 shown in FIG. 8, the strip portion 5.1 has a free end portion defining a surface facing toward the ramp 11 which is an inclined planar surface constituting a ramp 26, limited toward the interior of the hook by a transverse edge 27. The curved surface 28 leading from this edge 27 is limited on the opposite side by a second edge 29 extending along a transverse generatrix. Consequently, a rod 31 of sufficient diameter can only be supported on the two parallel edges 27, 29, in which position it is clamped by the clamping screw 14. On the other hand, a rod 32 of smaller diameter corresponding to the curvature of the surface 28, can be completely applied against the latter in consequently filling the empty space 33 defined between the surface 28 and the rod 31. The illustrated rods 31 and 32 are smooth but of course may have asperities on the surface.

The profile of the strip portion 5.1 has the advantage of facilitating the correct positioning in a substantially automatic manner of the rod in the hook 20.1 during some surgical operations when special difficulties of the positioning of the rod are encountered.

The profile of the support surface 28 may also be of interest if it is desired to standardize the design of the hook for different rod diameters.

Figure 9:
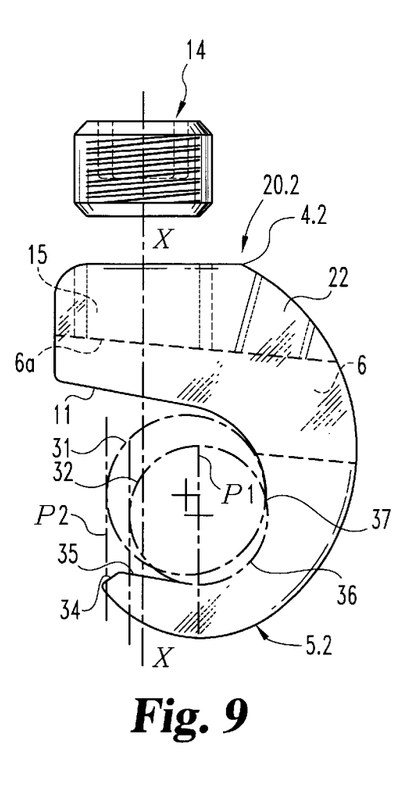

In the alternative embodiment shown in FIG. 9, the free end portion of the strip portion 5.2 of the hook 20.2 defines a first transverse inclined ramp 34 followed by a second longer ramp 35 having a smaller inclination than the ramp 34 and connected to the circular surface 36 which is connected on the opposite side to a third planar ramp 37 connected through a connection region to the ramp 11. This profile of the strip portion 5.2 is also adapted to receive rods 31, 32 . . . of different diameters, the positioning of which is facilitated by the succession of inclined planar surfaces 34 and 35. it will be understood that the positioning of the planes P1, P2 and of the axis X—X referred to with reference to FIG. 10, is also valid for all the other described and illustrated embodiments.

In an alternative embodiment, ramps such as 26, 34, 35, 41 can be provided on the free end portions of the hook 1 shown in FIGS. 1 to 4.

As shown in FIG. 10, the tapped hole 15 and the clamping screw 14 are so positioned in the body of the hook that the axis X—X of the screw is located between an axial plane P1 of the rod 31 (or 2 . . . ) parallel to the axis X—X and a plane P2 tangent to the part of the surface of the rod 31 (2 . . . ) located in the opening of the hook 20. The tangent plane P2 is parallel to the axis X—X of the screw and to the axial plane P1. Advantageously, the axis X—X is located at about two-thirds of the distance between the two planes P1 and P2 as measured from the axial plane P1.

The strip portion 5.3 of the hook 20 shown in FIG. 10 has a ribbed inner surface 38 constituted by a succession of transverse and parallel serrations 39. This serrated surface 38 is connected to a planar ramp 41 forming the inner surface of the free end portion of the hook 5.3. Further, as an alternative arrangement, the tapped hole 22 may receive an additional clamping screw 42 for clamping the transverse bar in the hook and on the rod, after unscrewing the screw threaded portion 23 of the accessory 24.

Likewise, the tapped hole 15 may be arranged in the same way as the tapped hole 22 and receive a clamping screw identical to the screw 42 (FIG. 10).

FIG. 10 shows a smooth rod 31 placed in the hook 20, but it will be understood that this rod may be advantageously replaced by a rod 2 having asperities (FIGS. 5 and 6), the connection then being rendered more firm.

The following points should be noted:

In the various described embodiments, the rod is easily engaged in the strip portion of the hook until it reaches the bottom thereof. The presence of terminal access ramps such as 26, 34, 35, 41 on the free end portion of the strip portion of the hook, the inclination of which is oriented toward the interior of the strip portion, markedly facilitates placing the rod 2, 31 . . . in position. The rod is then subjected to the radial pressure exerted by the transverse bar 3 upon the tightening of the screw 14. The bar 3 under the effect of the clamping force exerted by the screw 14 urges the rod into the hollow portion of the strip portion 5, 5.1 . . . , so that the rod 2, 31 . . . is automatically correctly positioned in the hook.

The effectiveness of the connection between the component parts of the device is also ensured by the positioning of the clamping screw 14 in the end portion of the body 4, 4.1, 4.2, 4.3 of the hook. The axis X—X of the screw 14 is indeed located, in accordance with the diameter of the rod employed, more or less close to the tangent plane P2. Thus, the clamping action of the screw 14 on the hook, and therefore on the strip portion 5, 5.1 . . . , exerts forces which tend to slightly pivot the hook and its strip portion about the rod, and to maintain the latter within the strip portion 5, 5.1 . . . . These forces create slight irreversible deformations on the transverse bar 3 and on the rod 2, 31, 32 . . . which ensure the perenniality of the connection and guarantee its correct performance over a period of time.

Another important advantage of the various embodiments described resides in the solidity of the connection achieved between the rod and the hook, owing to the closure of the strip portion of the hook onto the rod after a complete assembly of the device. Indeed, when the transverse connection device is placed in positions the distance f between the lower face of the transverse bar 3 and the free end portion of the strip portion 5 or 5.1, 5.2, 5.3 . . . is less than the diameter of the rod 2, 31, 32 . . . , irrespective of the diameter of this rod. Consequently, if the rod can easily enter the hook, it cannot leave it after clamping with the screw 14, which guarantees safety in use of the device.

This safety is still further increased by the use of a rod having asperities, such as the rod 2, since upon the clamping and under the effect of the forces exerted on the asperities by the hook, they penetrate the metal of the bar 3 and remain clamped therein to prevent rotation and translation.

Figure 11:
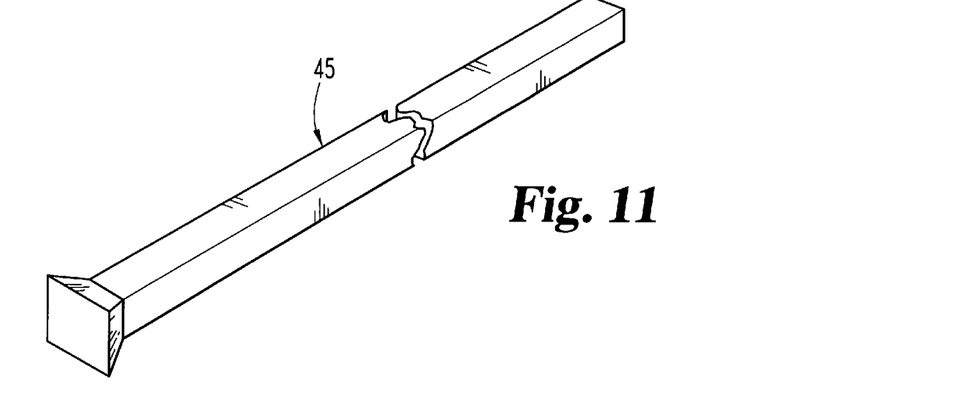
FIGS. 11, 12 and 13 are perspective views of three other embodiments of the transverse connection bar of the device according to the invention.
Figure 12:
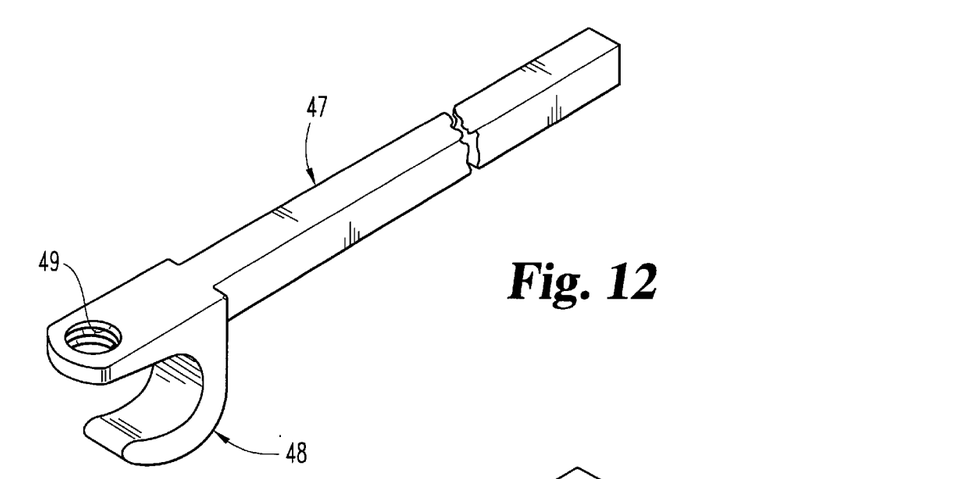
Figure 13:
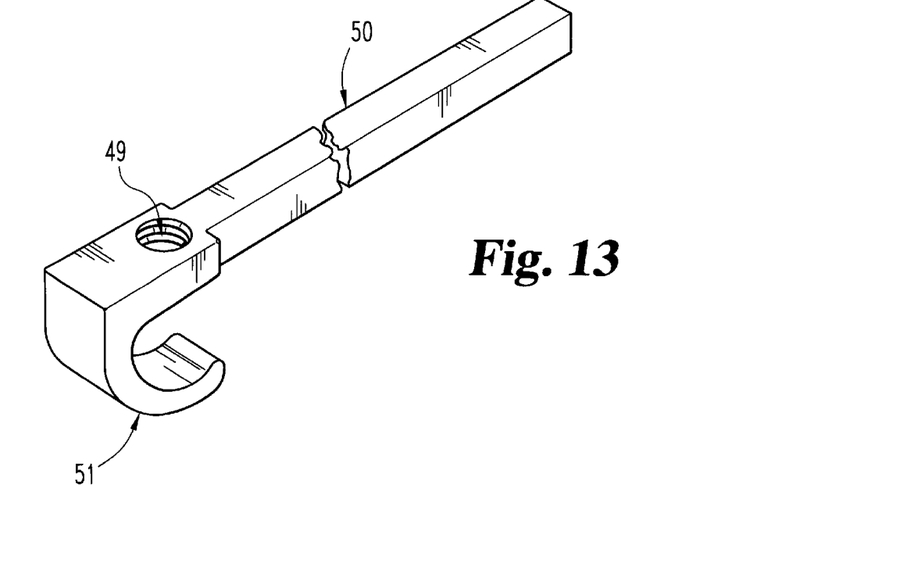

FIGS. 11 to 13 show three possible alternative embodiments of the transverse connection bar 3.

In FIG. 11, the bar 45 terminates at one end in an enlarged portion 46 which performs the function of a stop for one of the hooks. In FIG. 12, the bar 47 has one of its ends in the form of a hook 48 provided with an aperture 49 for receiving a screw such as the screw 14; the hook 48 is in one piece with the bar 47 and is oriented by spreading the rods 2 apart, as in FIG. 5.

In FIG. 13, one of the ends of the bar 50 is in one piece with a hook 51 similar to the hook 48, but oriented by moving the osteosynthesis rods closer together, as illustrated in FIG. 6.

Figure 15:
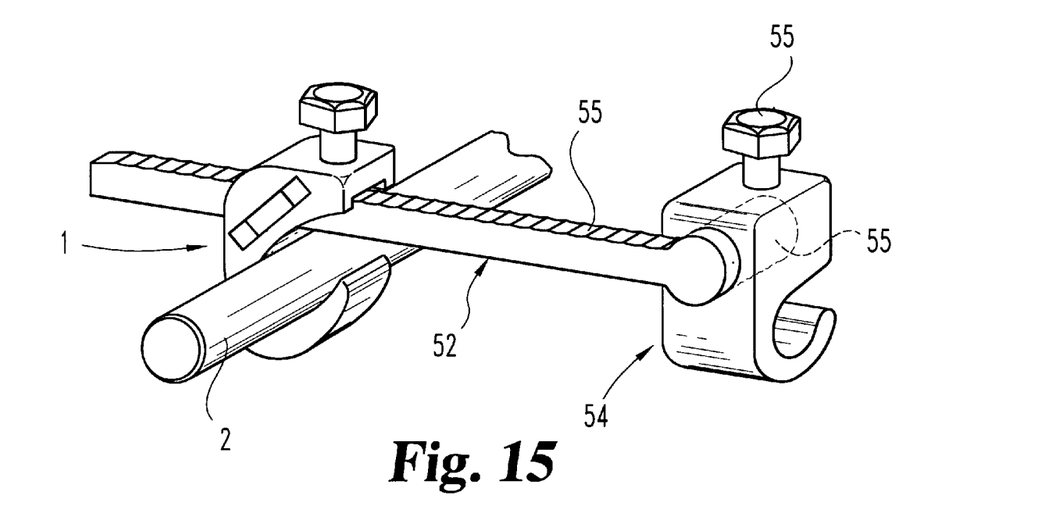
FIG. 15 is a perspective view of the assembly of an osteosynthesis rod and a vertebral anchorage member connected by means of a transverse bar according to FIG. 6.

The bar 3, 45 . . . may have asperities on the surface (in the manner of the Cotrel rods in FIG. 5), or be ribbed, etc., above all if the osteosynthesis rod in smooth, and in view of improving the fixation of the hook on this bar (as shown in FIG. 15).

It is understood that the present invention contemplates variation in the configuration of the elongated member (rod & transverse bar) and the hook. For example, the rod 2 and bar 3 may assume vaious cross-section shapes along their longitudinal length. The bar 3 may have a circular cross-section, for instance, which can be accommodated by a complementary modification to the aperture 7.

It is further contemplated that under certain circumstances the arrangement of rod and bar relative to the hook 1 may be changed. In such a case, the rod 2 may exend through aperture 7 while the bar 3 sits within region 13 of the hook, all portions of the hook being suitable configured.

Figure 14:
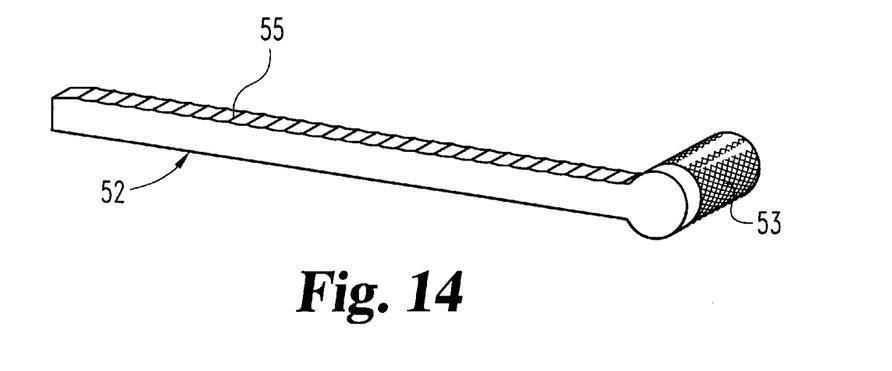
FIG. 14 is a perspective view of a further embodiment of the transverse bar of the assembly according to the present invention.

FIGS. 14 and 15 show a bar 52 having an end portion 53 that is cylindrical and perpendicular to the axis of the bar 52. This end portion 53 can receive an anchorage member 54 such as a hook, as illustrated, or a screw attached to end portion 53 by a fixation screw 56. The opposite end portion of bar 52 is attached to rod 2 by a hook 1 as described above.

As previously mentioned, the bar 52 can be smooth or provided with surface asperities such as ridges 55 on only one face (as shown) or on several faces to enhance fixation by hook 1. Additionally, bar 52 can have a rectangular, circuar or other cross-section.

What is claimed is:

1. A method for assembling a spinal osteosynthesis system, comprising:

mounting a spinal rod along a patient's spine;

providing a rigid transverse bar and a hook, the hook having a body with a curved strip portion extending from the body, the body defining a passage and a tapped hole intersecting the passage, the passage extending through the body and terminating in an aperture having a height exceeding the thickness of the bar;

receiving the bar in the passage, the bar passing through the aperture;

positioning the spinal rod in the curved strip portion;

engaging the tapped hole with a set screw;

tilting the bar about the spinal rod by turning the set screw to contact the bar after said receiving, said positioning, and said engaging; and tightening the screw after said tilting to clamp the bar against the spinal rod and the body of the hook.

2. The method of claim 1, wherein said strip portion has a first curved region with a first radius of curvature and a second curved region with a second radius of curvature different from the first radius of curvature.

3. The method of claim 1, wherein the passage defines a pair of edge portions in the body so shaped as to define a pair of ramps inclined toward the curved strip portion and said positioning further includes sliding the spinal rod along the ramps.

4. The method of claim 1, wherein said bar includes a first end portion configured to be received in said passage and a second end portion opposite the first end portion, the second end portion being integrally formed in a hook shape to receive another rod.

5. The method of claim 1, wherein the bar bears against the body in an upper part of the passage after said tightening.

6. The method of claim 1, wherein the hook includes an accessory hole intersecting the passage.

7. The method of claim 6, further comprising engaging the accessory hole with a threaded end portion of an accessory.

8. The method of claim 1, wherein the curved strip portion includes a ribbed inner surface.

9. The method of claim 1, wherein the bar terminates in a hook shape at one end.

* * * * *